United States Patent [19]

Cremer et al.

[11] Patent Number: 5,254,771

[45] Date of Patent: Oct. 19, 1993

[54] PROCESS FOR THE PREPARATION OF 1,1,1-TRIFLUORO-2-2-DICHLOROETHANE UNDER ELEVATED PRESSURE

[75] Inventors: Hans R. Cremer, Kerpen; Günter Siegemund, Hofheim am Taunus; Wilhelm Lendle, Bad Soden am Taunus, all of Fed. Rep. of Germany

[73] Assignee: Hoechst Aktiengesellschaft, Frankfurt, Fed. Rep. of Germany

[21] Appl. No.: 23,864

[22] Filed: Feb. 26, 1993

Related U.S. Application Data

[63] Continuation of Ser. No. 839,054, Feb. 18, 1992, abandoned, which is a continuation of Ser. No. 551,891, Jul. 12, 1990, abandoned.

[30] Foreign Application Priority Data

Jul. 14, 1989 [DE] Fed. Rep. of Germany ....... 3923248

[51] Int. Cl.$^5$ ............................................. C07C 17/00
[52] U.S. Cl. ..................................................... 570/123
[58] Field of Search ......................................... 570/123

[56] References Cited

U.S. PATENT DOCUMENTS

| | | |
|---|---|---|
| 2,473,162 | 6/1949 | McBee et al. ............... 570/252 |
| 2,861,032 | 11/1958 | Scherer et al. . | 
| 3,755,477 | 8/1973 | Firth et al. . |
| 4,060,469 | 11/1977 | Sweeney et al. . |
| 4,145,368 | 3/1979 | Sweeney et al. .............. 570/123 |
| 4,192,822 | 3/1980 | Sweeney et al. . |
| 4,614,572 | 9/1986 | Holbrook et al. . |

FOREIGN PATENT DOCUMENTS

0904831 8/1962 United Kingdom .

OTHER PUBLICATIONS

McBee, E. T. et al., Ind. and Eng. Chem. 39:409–411 (1947).

Georg–Thieme Verlag, Stuttgart, Germany (4th Ed. 1962) p. 596.

*Primary Examiner*—Alan Siegel
*Attorney, Agent, or Firm*—Connolly and Hutz

[57] ABSTRACT

The invention relates to a process for the preparation of 1,1,1-trifluoro-2,2-dichloroethane by chlorinating 1,1,1-trifluoro-2-chloroethane, in which the chlorination is carried out under an elevated pressure. The pressure is preferably 10 to 400 bar, particularly 50 to 250 bar. If the reaction is initiated by heat, it is preferably carried out at 200° to 300° C. If it is initiated by a free-radical starter, the reaction is preferably carried out at 150° to 250° C.

17 Claims, No Drawings

PROCESS FOR THE PREPARATION OF 1,1,1-TRIFLUORO-2-2-DICHLOROETHANE UNDER ELEVATED PRESSURE

This application is a continuation of U.S. patent application Ser. No. 07/839,054, filed on Feb. 18, 1992, now abandoned, which in turn is a continuation of U.S. patent application Ser. No. 07/551,891, filed Jul. 12, 1990, now abandoned.

The invention relates to a process for the preparation of 1,1,1-trifluoro-2,2-dichloroethane (R 123) by chlorinating 1,1,1-trifluoro-2-chloroethane (R 133a). 1,1,1-Trifluoro-2,2-dichloroethane (R 123) is considered a potential replacement for the completely halogenated chlorofluorocarbon fluorotrichloromethane (R 11), the production and consumption of which must be restricted because it is suspected of damaging the ozone layer. R 123 makes a smaller contribution to the greenhouse effect and, by virtue of its degradation behavior in the lower layers of the atmosphere, is a considerably lower potential ozone hazard. Its main use is as a foaming agent in the processing of plastics and as a cleansing agent.

1,1,1-Trifluoro-2,2-dichloroethane ($CF_3$-$CHCl_2$) is obtained in accordance with U.S. Pat. No. 3,755,477 by reacting perchloroethylene with anhydrous hydrogen fluoride at temperatures of 360° C. over chromium catalysts. Disadvantages in this process are not only the rapid deactivation of the catalysts, but also the low yield of $CF_3$-$CHCl_2$ and the large number of by-products of no commercial use. In addition, the formation of dichlorotrifluoroethane isomers (for example R 123a) which are questionable from a toxicological point of view and cannot be removed by distillation, cannot be excluded in this procedure.

A further method of preparing 1,1,1-trifluoro-2,2-dichloroethane is the photochlorination, described in U.S. Pat. No. 4,060,469, of 1,1,1-trifluoro-2-chloroethane in the gas phase. Disadvantages in this process are the very low light quantum yield and the low conversion. According to U.S. Pat. No. 4,145,368 and US-A 4,192,822, the yield of R 123 can certainly be increased if the reaction products are passed over chromium oxyfluoride catalysts at 350° C. However, even in this process variant, the yield can only be raised to a maximum of 14 %. An additional factor is not only that the CR-0-F catalysts used catalyse the dismutation reaction, but also that dismutation, isomerization and elimination reactions take place over these catalysts and by-products of no commercial use are therefore produced to a considerable extent in this procedure.

It is also known that 1,1,1-Trifluoro-2,2-dichloroethane is accessible via the thermal chlorination of 1,1,1-trifluoroethane. As reported by E.T. McBee et al., Ind. and Engineering Chem., 39, pages 409-411 (1947), 1,1,1-trifluoroethane is reacted at 497° C with a 1:1-molar ratio of chlorine (page 411 and Table III). However, this process is unsuitable for the industrial preparation of R 123, since less than half the chlorine employed reacts, and, under the reaction conditions, R 123 is only a byproduct in the mixture of products. Under the conditions indicated, not only the completely halogenated main product $CF_3$-$CCl_3$, but also undesirable degradation products (for example $CCl_4$ and $CF_3Cl$) are found in the product spectrum.

It was therefore an object to provide a process for the efficient and economical preparation of 1,1,1-trifluoro-2,2-dichloroethane which can be carried out advantageously on an industrial scale.

The invention relates to a process for the preparation of 1,1,1-trifluoro-2,2-dichloroethane by chlorinating 1,1,1-trifluoro-2-chloroethane, which comprises carrying out the chlorination under an elevated pressure.

Under normal pressure, the chlorination of 1,1,1-trifluoro-2-chloroethane generally only takes place at temperatures above 380° C. and even then only incompletely. It was therefore all the more surprising to find that the chlorination of 1,1,1-trifluoro-2-chloroethane can be carried out, by the application of an elevated pressure, at much lower reaction temperatures and with high conversion rates and a high selectivity of conversion.

1,1,1-Trifluoro-2,2-dichloroethane is obtained in the process according to the invention in a form free from isomers, and virtually the only by-product obtained is 1,1,1-trifluoro-2,2,2-trichloroethane. Thus neither undesirable degradation reactions (C—C cleavage reactions) nor other interfering side reactions take place in this case.

Compared with chlorination without the use of pressure, carrying out the reaction under pressure in accordance with the present invention has the advantage that, in addition to higher selectivity of conversion, the conversion is substantially greater and higher time yields can be achieved. The chlorine employed reacts completely and therefore does not need to be removed subsequently from the product mixture.

It is preferable to use pressures of 10 to 400 bar, in particular 50 to 250 bar for carrying out the process.

The reactants can be present in a supercritical or liquid state in the process according to the invention.

It is also possible to carry out the chlorination in an inert solvent which forms the liquid phase, as a result of which the pressure and the temperature can, of course, be varied within a somewhat wider range than when the reaction is carried out without a solvent, and an advantageous dilution effect can be achieved.

It is advantageous, in this case, to employ solvents whose critical temperatures are above the reaction temperatures used and which are inert under the conditions of chlorination. Chlorinated hydrocarbons, fluorinated hydrocarbons and chlorofluorocarbons are particularly advantageous, preferably carbon tetrachloride and trichlorotrifluoroethane.

The reaction can be started (initiated) thermally or chemically.

In the case of thermal initiation, the reaction is generally carried out at temperatures from 150° to 400° C, preferably 200° to 300° C. In the case of chemical initiation, the reaction is generally carried out at temperatures from 100° to 300° C, preferably 150° to 250° C.

In the case of chemical initiation, the initiators known for chlorinations are used. For example, diazo compounds, such as 2,2'-azoisobutyrodinitrile, or peroxide compounds, such as lauryl peroxide and benzoyl peroxide, can be used in this case.

The process achieves very good conversions at amounts of initiator from $1 \times 10^{-2}$ to $1 \times 10^{-6}$, preferably from $1 \times 10^{-3}$ to $1 \times 10^{-5}$, mol of initiator per mol of chlorine. Higher concentrations of initiator (free-radical initiator) are possible, but are not necessary for the good progress of the process.

The present process can be carried out either continuously or discontinuously. When the reaction is carried out discontinuously, the chlorine is introduced into the pressure reactor in a gaseous or liquid state and the 1,1,1-trifluoro-2-chloroethane is introduced in a liquid state, with or without a solvent. If free-radical initiators are used, they can be added directly to the pressure vessel, but preferably they are dissolved in 1,1,1-trifluoro-2-chloroethane or, if appropriate, in the solvent. The corresponding reaction pressure is determined by the amounts of starting materials and the reaction temperature. When the process is operated continuously, the pressure is, apart from the effect of temperature, generated by pumping in the reactants and is kept constant by means of a relief valve.

After leaving the reactors, the products are depressurized, the anhydrous hydrogen chloride formed is removed, and the residue is rectified, it being possible to recycle and to employ again the unreacted 1,1,1-trifluoro-2-chloroethane.

Nickel has proved suitable as a reactor material. Pure nickel is preferable, but steels and special alloys of high nickel content are also used as materials.

Various forms of reactors are possible when the process according to the invention is used on an industrial scale. For example, it is possible to employ stirred kettles, cascade reactors and tubular reactors, preferably tubular reactors.

The chlorine/R 133a molar ratio should generally be about 0.02–1.0. If a high selectivity of conversion is desired, it is preferable to select a molar ratio of 0.02–0.4. If, on the other hand, a high conversion is desired, it is preferable to select a molar ratio of 0.4–1.0.

The invention is illustrated in greater detail in the following examples.

The product compositions were analyzed by gas chromatography and, in addition, identified by $^{19}$F-spectroscopy and $^{1}$H-NMR-spectroscopy. The percentages quoted are percentages by weight.

EXAMPLE 1

An autoclave of 1 liter capacity, lined with pure nickel, was charged, while moisture was excluded, with the amounts of 1,1,1-trifluoro-2-chloroethane and chlorine shown in Table 1. The autoclave was brought to the desired reaction temperature by means of jacket heating and the internal temperature in the reactor was kept constant during the test. After this, the reactor was cooled to room temperature and the pressure was released. After the hydrogen chloride had been removed, the products were characterized and worked up by distillation.

The results of the tests are shown in Table 1.

TABLE 1

| | | Chlorine/R 133a molar ratio | | |
|---|---|---|---|---|
| | | 0.27 | 0.51 | 0.58 |
| Temperature: | (°C.) | 250 | 250 | 250 |
| Pressure: | (bar) | 120 | 127 | 122 |
| Reaction time: | (hrs) | 1 | 1 | 1 |
| Starting materials: | | | | |
| $CF_3$—$CH_2Cl$ | (g) | 280 | 237 | 225 |
| Chlorine | (g) | 45 | 72 | 78 |
| Products: | | | | |
| $CF_3$—$CH_2Cl$ | (%) | 70.1 | 51.5 | 47.0 |
| $CF_3$—$CHCl_2$ | (%) | 24.9 | 35.0 | 36.0 |
| $CF_3$—$CCl_3$ | (%) | 4.7 | 13.5 | 17.0 |
| Other | (%) | <0.1 | <0.1 | <0.1 |
| Conversion: | | | | |
| Chlorine | (%) | >99 | >99 | >99 |
| R 133a | (%) | 24.4 | 40.9 | 45.1 |
| Selectivity of conversion: | | | | |
| R 123 | (%) | 83.3 | 72.2 | 67.9 |

EXAMPLE 2

2 mol of carbon tetrachloride were initially placed, as an inert solvent, in the pressure vessel described in Example 1, and the starting materials 1,1,1-trifluoro-2-chloroethane and chlorine were metered in. Good mixing of the reactants was ensured during the heating up period and the reaction time by means of a shaking device. The products were worked up by distillation after the expiry of the reaction time in each case.

The results are listed in Table 2.

TABLE 2

| | | Chlorine/R 133a molar ratio | |
|---|---|---|---|
| | | 0.26 | 0.58 |
| Temperature: | (°C.) | 200 | 220 |
| Pressure: | (bar) | 62 | 70 |
| Reaction time: | (hrs) | 3 | 1 |
| Starting materials: | | | |
| $CF_3$—$CH_2Cl$ | (g) | 280 | 280 |
| Chlorine | (g) | 43 | 40 |
| Solvent: | | | |
| $CCl_4$ | (g) | 363 | 363 |
| Products: | | | |
| (excluding carbon tetrachloride) | | | |
| $CF_3$—$CH_2Cl$ | (%) | 70.9 | 73.0 |
| $CF_3$—$CHCl_2$ | (%) | 25.0 | 23.4 |
| $CF_3$—$CCl_3$ | (%) | 4.0 | 3.5 |
| Other | (%) | <0.1 | <0.1 |
| Conversion: | | | |
| Chlorine | (%) | >99 | >99 |
| R 133a | (%) | 23.7 | 21.8 |
| Selectivity of conversion: | | | |
| R 123 | (%) | 85.9 | 86.7 |

EXAMPLE 3

100 mg of 2,2'-azoisobutyrodinitrile were dissolved in 2 mol of carbon tetrachloride, and the solution was introduced into the autoclave described in Example 1. 1,1,1-Trifluoro-2-chloroethane and chlorine were then added, and then the reaction was carried out at 180° C. After the products had been worked up, the results were as follows:

TABLE 3

| | | Chlorine/R 133a molar ratio | |
|---|---|---|---|
| | | 0.26 | 0.58 |
| Temperature: | (°C.) | 180 | 180 |
| Pressure: | (bar) | 50 | 55 |
| Reaction time: | (hrs) | 1 | 1 |
| Starting materials: | | | |
| $CF_3$—$CH_2Cl$ | (g) | 280 | 237 |
| Chlorine | (g) | 43 | 64 |
| Free-radical initiator: | (mg) | 100 | 100 |
| (2,2'-azoisobutyrodinitrile) | | | |
| Solvent: | | | |
| $CCl_4$ | (g) | 363 | 363 |
| Products: | | | |
| (excluding carbon tetrachloride) | | | |
| $CF_3$—$CH_2Cl$ | (%) | 71.6 | 53.9 |

TABLE 3-continued

|  |  | Chlorine/R 133a molar ratio | |
|---|---|---|---|
|  |  | 0.26 | 0.58 |
| $CF_3-CHCl_2$ | (%) | 24.3 | 34.3 |
| $CF_3-CCl_3$ | (%) | 4.0 | 11.8 |
| Other | (%) | <0.1 | <0.1 |
| Conversion: |  |  |  |
| Chlorine | (%) | >99 | >99 |
| R 133a | (%) | 23.0 | 38.8 |
| Selectivity of conversion: |  |  |  |
| R 123 | (%) | 85.6 | 74.4 |

We claim:

1. A process for the preparation of 1,1,1-trifluoro-2,2-dichloroethane by chlorinating 1,1,1-trifluoro-2-chloroethane, which comprises thermally initiating the chlorination and carrying out said chlorination at temperatures from 150° to 400° C. and under an elevated pressure in a reaction mixture which is present in a supercritical state or in the liquid phase, said elevated pressure ranging from about 50 to about 400 bar.

2. The process as claimed in claim 1, wherein the liquid phase is maintained by means of pressure.

3. The process as claimed in claim 1, wherein the liquid phase is formed by a solvent.

4. The process as claimed in claim 3, wherein the solvent employed is a chlorinated hydrocarbon, a fluorinated hydrocarbon or a chlorofluorocarbon.

5. The process as claimed in claim 4, wherein the solvent employed is carbon tetrachloride or 1,1,1-trifluoro-2,2,2-trichloroethane.

6. The process as claimed in claim 1, wherein the reaction is carried out at pressures of 50 to 250 bar.

7. The process as claimed in claim 1, wherein the chlorine/1,1,1-trifluoro-2-chloroethane molar ratio is between 0.02 and 1.0.

8. The process as claimed in claim 1, wherein the reaction is carried out continuously.

9. The process as claimed in claim 1, wherein the reaction is carried out in a tubular reactor.

10. A process for the preparation of 1,1,1-trifluoro-2,2-dichloroethane by chlorinating 1,1,1-trifluoro-2-chloroethane, which comprises carrying out the chlorination under an elevated pressure in a reaction mixture which is present in a supercritical state or in the liquid phase, said elevated pressure ranging from 50 to 400 bar.

11. The process as claimed in claim 10, wherein the chlorination is initiated by free-radical initiators and is carried out at temperatures from 100° to 300° C.

12. The process as claimed in claim 10, wherein the chlorination is initiated by free-radical initiators and is carried out at 150° to 250° C.

13. The process as claimed in claim 11, wherein the free-radical initiator used is a diazo compound or a peroxide compound.

14. The process as claimed in claim 12, wherein the free-radical initiator used is a diazo compound or a peroxide compound.

15. The process as claimed in claim 11, wherein 2,2'-azoisobutyrodinitrile is used as the free-radical initiator.

16. The process as claimed in claim 12, wherein 2,2'-azoisobutyrodinitrile is used as the free-radical initiator.

17. The process as claimed in claim 1, wherein said reaction is initiated thermally and said reaction is carried out at temperatures from 200° to 300° C.

* * * * *